(12) United States Patent
Wu et al.

(10) Patent No.: US 8,883,689 B2
(45) Date of Patent: Nov. 11, 2014

(54) STABILIZED HERBICIDAL COMPOSITIONS

(75) Inventors: Tai-Teh Wu, Chapel Hill, NC (US);
Karen L. Eagles, Raymore, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 1150 days.

(21) Appl. No.: 11/509,283

(22) Filed: Aug. 24, 2006

(65) Prior Publication Data

US 2007/0129251 A1 Jun. 7, 2007

Related U.S. Application Data

(63) Continuation-in-part of application No. 11/295,757, filed on Dec. 6, 2005, now abandoned.

(51) Int. Cl.
| A01N 43/76 | (2006.01) |
| A01N 25/04 | (2006.01) |
| A01N 25/16 | (2006.01) |
| A01N 43/56 | (2006.01) |

(52) U.S. Cl.
CPC ............... A01N 43/56 (2013.01); A01N 43/76 (2013.01)
USPC ........... 504/270; 504/139; 504/103; 504/138; 504/282; 504/106; 548/365.1; 548/369.4

(58) Field of Classification Search
CPC ... A01N 43/76; A01N 43/56; A01N 2300/00; A01N 25/22; A01N 33/12
USPC ......... 504/138, 139, 103, 270, 282, 106, 128, 504/365; 548/365.1, 369.4
See application file for complete search history.

(56) References Cited

U.S. PATENT DOCUMENTS

| H001942 H | 2/2001 | Theodoridis et al. | |
| 6,746,988 B2* | 6/2004 | Hopkinson et al. | ........... 504/127 |
| 6,908,883 B2 | 6/2005 | Sievernich et al. | |
| 2002/0042345 A1* | 4/2002 | Kocur et al. | .................. 504/211 |
| 2004/0106519 A1* | 6/2004 | Ruegg | ........................... 504/221 |
| 2007/0129251 A1 | 6/2007 | Wu et al. | |
| 2007/0259789 A1 | 11/2007 | Huchet et al. | |

FOREIGN PATENT DOCUMENTS

| RU | 2 260 947 C1 | | 9/2005 |
| WO | WO 98/24321 | * | 6/1998 |
| WO | WO 0078139 A2 | * | 6/2000 |
| WO | 2007/067472 | | 6/2007 |

OTHER PUBLICATIONS

Gaillard et al. ,FEBS Letters 352,1994,219-221.*

* cited by examiner

*Primary Examiner* — Janet Epps-Smith
*Assistant Examiner* — Courtney Brown

(57) ABSTRACT

A herbicide composition includes a fenoxaprop ester and a weak acid buffer system. The buffer system maintains the herbicidal composition at a pH in the range of 4 to 8. In one non-limiting embodiment, the fenoxaprop ester is fenoxaprop ethyl. The buffer system can include an amine-containing material, such as a tertiary amine. The herbicide composition can include other herbicides, such as weak acid herbicides, for example pyrasulfotole, bromoxynil, and/or bromoxynil esters and can include one or more safeners.

20 Claims, 1 Drawing Sheet

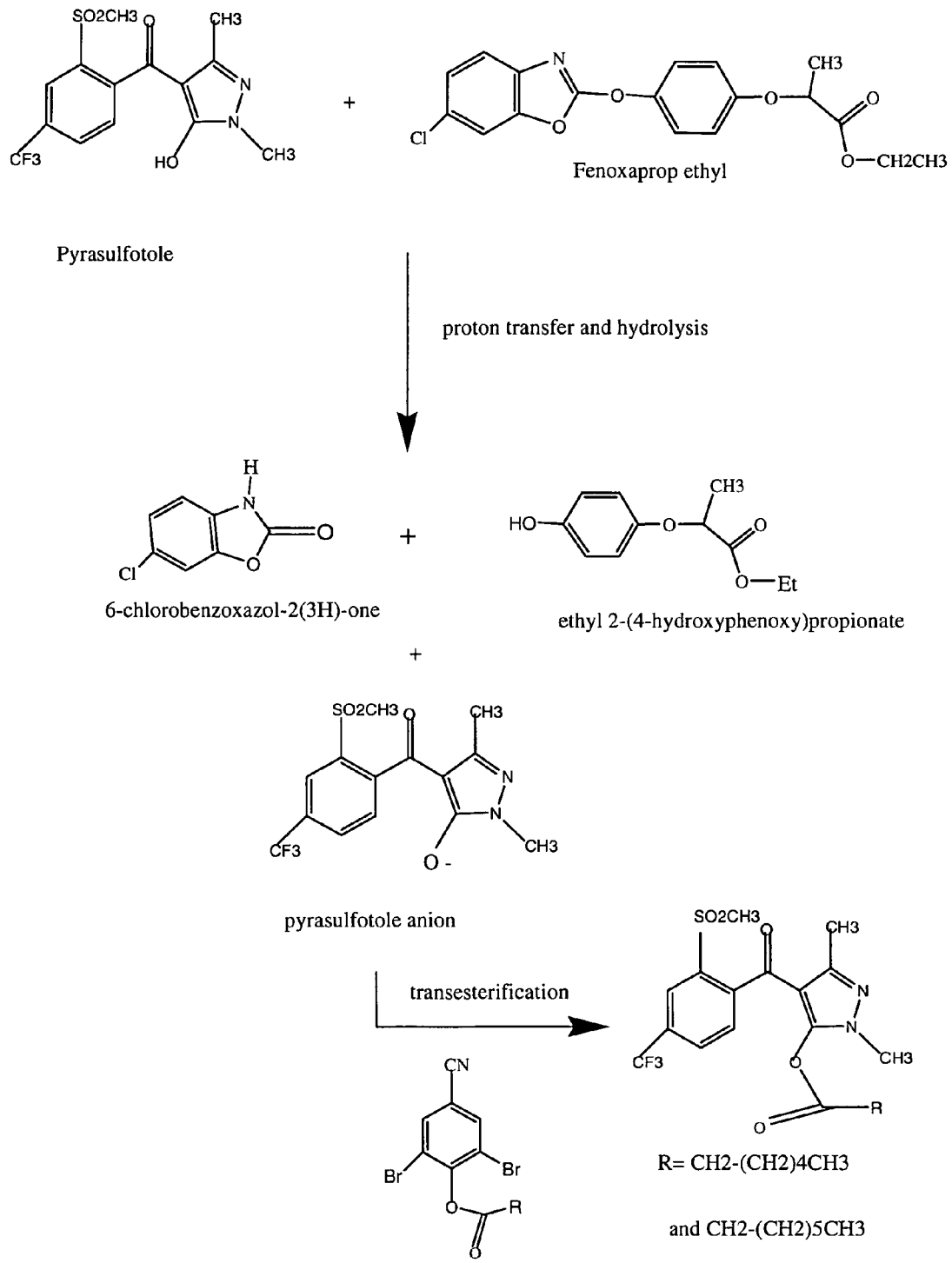

STABILIZED HERBICIDAL COMPOSITIONS

This is a continuation-in-part of U.S. application Ser. No. 11/295,757, filed Dec. 6, 2005, now abandoned.

BACKGROUND OF THE INVENTION

1. Field of the Invention

The present invention relates generally to crop protection compositions and, in one embodiment, to crop protection compositions containing aryloxyphenoxypropionic esters and uses thereof.

2. Description of the Current Technology

A wide variety of herbicides are in use today. These known herbicides can be effective against different types of undesirable vegetation and can act in different ways. For example, some herbicides are particularly useful when applied to broad leaf plants while others are more useful when applied to grassy plants. Also, these different herbicides can perform their herbicidal function in different ways. For example, some herbicides may act as acetyl-CoA carboxylase inhibitors while others act in a completely different manner, such as acetolactate synthase inhibitors, or carotenoid biosynthesis inhibitors, or mitosis inhibitors, or photosynthesis inhibitors, just to name a few. In order to combat a wide variety of different types of undesirable vegetation, it is not uncommon to combine several different types of herbicides into a single herbicidal composition. This herbicidal composition can then be applied to a field in a single application without having to apply each of the herbicides individually.

An example of one particularly useful group of herbicides are aryloxyphenoxypropionic esters. Aryloxyphenoxypropionic esters typically act as acetyl-CoA carboxylase inhibitors. An example of such herbicides include fenoxaprop esters, such as fenoxaprop ethyl, commercially available from Bayer CropScience, LP. The fenoxaprop esters, such as fenoxaprop ethyl, are particularly useful for application to cereal crops to combat grassy weeds. A basic formula for fenoxaprop herbicides is shown in Formula I below.

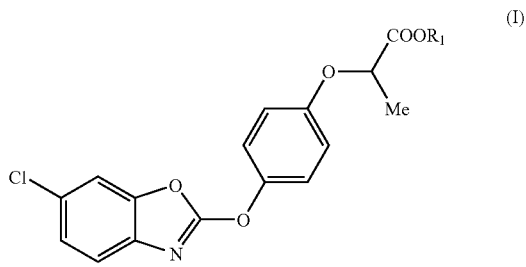

$R_1$ = H: fenoxaprop
$R_1$ = $CH_2CH_3$: fenoxaprop-ethyl

The fenoxaprop ester herbicides are quite well adapted for application to cereal crops and have found widespread acceptance. However, it has been observed that when a fenoxaprop ester herbicide, particularly fenoxaprop ethyl or a fenoxaprop lower alkyl ester, is mixed with certain other herbicides, the fenoxaprop ester herbicide can degrade more rapidly that if the fenoxaprop herbicide were not mixed with the other herbicides. This has been particularly observed when a fenoxaprop ester is mixed with herbicides that act as weak acids, such as pyrasulfotole and bromoxynil. This increased degradation of fenoxaprop esters can be disadvantageous to a farmer because it can decrease the useful shelf life of a fenoxaprop ester containing herbicidal composition. See FIG. 1 for example.

Therefore, it would be useful to provide a fenoxaprop ester containing herbicidal composition that reduces or eliminates the drawbacks associated with previous herbicidal compositions.

SUMMARY OF THE INVENTION

A herbicide composition comprises a fenoxaprop ester and a buffer system. The buffer system maintains the herbicidal composition at a pH in the range of 4 to 8, such as 4.5 to 8, such as 5 to 7.5, such as 5.8 to 7.5. In one non-limiting embodiment, the fenoxaprop ester is fenoxaprop ethyl. The buffer system can comprise an amine-containing material, such as a tertiary amine. The herbicide composition can include other herbicides, such as weak acid herbicides, and can include one or more safeners.

BRIEF DESCRIPTION OF THE DRAWINGS

FIG. 1 is a schematic representation of the acid-catalyzed hydrolysis and transesterification reaction mechanism of the present invention.

DESCRIPTION OF THE PREFERRED EMBODIMENTS

As used herein, all numbers, such as but not limited to dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims may vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.5, 5.5 to 10, 2.3 to 7.3, etc. All references and publications referred to herein, such as but not limited to U.S. patents and published applications, are to be understood as being herein incorporated by reference in their entirety.

In one non-limiting embodiment, a herbicidal composition of the invention comprises a aryloxyphenoxypropionic ester, such as a fenoxaprop ester herbicide (optically active or racemic mixture), a buffer system, optionally one or more weak acid herbicides, and optionally one or more safeners.

Aryloxyphenoxypropionic esters have been described above. Non-limiting examples of aryloxyphenoxypropionic esters are described, for example, in U.S. Pat. Nos. 6,908,883 B2 and 6,887,827 B2. The present invention will be described with respect to the use of a fenoxaprop ester, such as fenoxaprop ethyl, in a herbicide composition. However, it is to be understood that the invention is not limited to use with fenoxaprop ethyl but is believed to be applicable to other aryloxyphenoxypropionic esters, e.g., fenoxaprop esters.

The buffer system can be a weak acid buffer system and can comprise a water-miscible acid and a water-miscible salt of the acid. In a highly advantageous embodiment of the invention, the water-miscible acid is a herbicide. By the term "weak acid" is meant an acid with a $pK_a$ in the range of 0.1 to 10 at 25° C. The buffer system is configured to maintain the pH of the herbicidal composition in the range of 4 to 10, e.g., 4 to 8, e.g., 4.5 to 8, e.g., 5 to 7.5, e.g., 5.8 to 7.5. For example, the buffer system could maintain the pH of the herbicide composition in the range of 4 to 7, such as 5 to 7, such as 5 to 6.

The salt of the weak acid can be an amine or imine salt of the weak acid. Substantially non-nucleophilic conjugate amines are preferred to prepare the amine salts. Tertiary alkyl amines are most preferred, although secondary alkyl amines and primary amines may be used. The amine can also comprise primary, secondary, and/or tertiary amine function in any combination within the same molecule or the mixture of them. For example, the amine can be a tertiary amine or a trialkylamine in which the alkyl can be optionally substituted with a hydroxy group.

Generally one or more of the alkyl moieties of the amine has from 1 to 50 carbons, preferably from 1 to 10 carbons, and, in an alternative embodiment, has from 2 to 6 carbons. The alkyl group can be straight chained, branched, or cyclic alkyl. The one or more alkyl moieties can be, independent of one another, optionally substituted by one or more ether groups, e.g. alkoxy, hydroxyl groups, thiol groups, alkylthio, alkene, alkyne, amino, alkylamino, dialkylamino, or combinations of these functional groups that include a carbon to carbon double bond (i.e., an alkene) or carbon to carbon triple bond (i.e., an alkyne). The amine can be in the form of monoamine or diamine or polyamine. In a preferred embodiment, the one or more alkyl moieties of the amine may be hydroxylated, ethoxylated, diethoxylated, triethoxylated, or substituted with hydroxyethoxy or hydroxypropoxy groups wherein the number of ethoxy and propoxy groups may be from 1 to 60.

The composition can be in any formulation form, particularly a liquid composition, such as an emulsifiable concentrate, suspoemulsion, suspension concentrate, or a solution, such as an aqueous solution. In one non-limiting embodiment, an emulsifiable concentrate and a suspoemulsion is preferred.

The conjugate base of the amine salt may also serve as a surfactant in the composition, such as a nonionic surfactant or an ionic surfactant.

Representative conjugate amines and imines include one or more of the following: tertiary amines such as triethanolamine, triisopropanolamine; trialkylamines such as triethylarnine, trimethylamine, tripropylamine, triisopropylamine, 1-octaneamine-N,N-dimethyl, N,N-dimethylcyclohexanamine, N,N-dimethyl-1-hexadecylamine, 1-dodeccanamine-N,N-dimethyl, ethyldiethanolamine, hexamethylenetetramine, N,N,N'',N''-tetrakis-(2-hydroxypropyl) ethylene diamine, dicocoalkyl-methylamine, didecylmethylamine, tridodecyamine; trihexadecylamine; monoalkyldimethylamines such as dodecyldimethylamine, hexadecyl-dimethylamine, octadecyl-dimethylamine, cocoalkyl-dimethylamine, soyalkyl-dimethylamine, soyaalkyl-dimethylamine, tallowalkyl-dimethylamine, hydrogenated tallowalkyl-dimethylamine, cottonseed alkyl-dimethylamine; ethoxylated alkylamines such as ethoxylated(n) cocoalkylamine, ethoxylated (n) tallowalkylamine, ethoxylated (n) soyaalkylamine, ethoxylated cottonseed amine, oleyl amine ethoxylate, ethoxylated(n) octadecylamine, (ethoxy group numbers n may be from 1 to 60), ethoxylated diamines, such as ethoxylated(n) N-tallow-1,3-diamineopropane, ethoxylated(n) N-tallow-1,3-diaminopropane, ethoxylated(n) N-tallow-1,3-diaminopropane, N,N-bis[α-ethyl-ω-hydroxypoly(oxyethylene)alkylamine; the poly (oxyethylene) content average 3 moles; the alkyl groups (C14-C18) are derived from tallow, or from soybean or cottonseed oil acids, or other crop or vegetable seeds oil acids. N,N-bis(2-hydroxyethyl)alkylamine, where the alkyl groups (C8-C 18) are derived from coconut, cottonseed, soya, or tallow acids or other crops or vegetable seed acids; N,N-Bis 2-(ω-hydroxypolyoxyethylene)ethyl)alkylamine; the reaction product of 1 mole N,N-bis(2-hydroxyethyl)alkylamine and 3-60 moles of ethylene oxide, where the alkylgroup (C8-C18) is derived from coconut, cottonseed, soya, or tallow acids or other crop or vegetable seed acids. N,N-Bis-2-(ω-hydroxypolyoxyethylene/polyoxypropylene)ethyl alkylamine; the reaction product of 1 mole of N,N-bis(2-hydroxyethyl alkylamine) and 3-60 moles of ethylene oxide and propylene oxide, where the alkyl group (C8-C18) is derived from coconut, cottonseed, soya, or tallow acids or other crop seeds or vegetable seeds acids, N,N'-Bis,(2-hydroxyethyl)-C12-C18 alkylamine, N,N'-bis(polyoxyethylene)cetylamine, N,N'-Bis(polyoxyethylene)oleylamine, N,N'-bis(polyoxyethylene)stearylamine, N,N'-dinitropentamethylenetetramine, ethoxylated abietylamine. Secondary amine such as diethylamine, diisopropanolamine, dimethylamine, ditallowamine, dicocoalkylamine, dehydrogenated tallowalkylamine, didecylamine, dioctadecylamine, ethylethanolamine. Primary amine such as ethanolamine, butylamine, ethylamine, oleylamine, isopropylamine, isopropanolamine, propylamine, dodecanamine, primary N-alkylamine, where the alkyl group (C8-C18) is derived from coconut, cottonseed, soya or tallow acids, polyoxyethylated primary amine (C14-C18); the fatty amine is derived from an animal source and contains 3% water, the poly(oxyethylene) content average 20 moles, amines, C14-C15 alkyl, ethoxylated, amines, C16-C18 and C18 unsaturated, alkyl, ethoxylated. amines, tallowalkyl, ethoxylated with polyethylene, triethylene tetramine, ethylendiamine, diethyleneamine, diethylenetriamine, N-oleyl-1,3-propanediamine, tetramethylene pentamine, polypropylene glycol bis(2-aminopropyl)ether, 2-[(2-aminoethyl)amino]ethanol, 2-amino-2-methyl-1-propanol. Imines such as N,N'-disalicylidene-1,2-diaminopropane.

The herbicidal composition can include one or more weak acids. Non-limiting examples of representative weak acids include the following: phenols, phenol esters and mixtures of phenols and phenol esters, substituted phenols, conjugated diketones, conjugated triketones, carboxylic acids or their salts, such as alkylcarboxylic acids, phenylcarboxylic acids, phenoxy acetic acids, phenoxy propionic acids and their substituted and branched analogs and ester analogs.

Non-limiting examples of representative weak acids that are agriculturally acceptable herbicides include the following: pyrazole herbicides such as pyrasulfotole, nitrile herbicides such as bromoxynil, chloroxynil, or ioxynil, or a propesticidal precursor thereof, for example, bromoxynil octanoate or bromoxynil heptanoate, 2,4-D, Dicamba, MCPA, MCPP (mecoprop), or MCPB.

The herbicide composition may also be an agriculturally acceptable safener, such as but not limited to mefenpyr, isoxadifen, fenchlorazole, or cloquintocet, just to name a few.

Fenoxaprop ethyl when mixed with a weak acid herbicide (like pyrasulfotole) tends to degrade, e.g., hydrolyze, over time. In order to combat this degradation, a buffer system in accordance with the invention is introduced to the composition. An amine-containing buffer system, such as triethanolamine, triethylamine, and/or triisopropanolamine, has been found to be particularly useful.

In one non-limiting embodiment, the composition comprises (by weight percent based on the total weight of the composition) 3 wt. % to 6 wt. % pyrasulfotole, 7 wt. % to 10 wt. % fenoxaprop-ethyl, 1 wt. % to 4 wt. % triethanolamine, and, optionally, 3 wt. % to 6 wt. % mefenpyr. The remainder of the composition can comprise fillers as are conventional in the art. The components can be emulsified and/or can be dissolved or dispersed in any conventional solvent.

EXAMPLE 1

An emulsifiable concentrate of fenoxaprop-ethyl, mefenpyr, and pyrasulfotole was prepared. Triethanolamine was selected as the buffer. The mixture of Table 1 was prepared by mixing the liquid ingredients, then the solid ingredients at 50° C.

TABLE 1

| INGREDIENTS |
| --- |
| Pyrasulfotole (99% pure) |
| Mefenpyr (94.8% pure) |
| fenoxyprop-ethyl (94% pure) |
| [1] alkyl alcohol ethoxylate |
| [2] castor oil ethoxylated |
| [3] benzene sulfonic acid, calcium salt |
| Propylene Carbonate |
| Triethanolamine |
| [4] aromatic organic solvent |

[1] Genopol X 060 alkylalcohol ethoxylate commercially available from Clariant Corporation.
[2] Emulsogen EL 400 commercially available from Clariant Corporation.
[3] Phenylsulfonate CA commercially available from Clariant Corporation.
[4] A150 commercially available from Exxon Corporation The mixture was tested for long-term storage stability by subjecting separate samples to different temperatures for eight weeks. The following test results were obtained and are shown in Table 2.

TABLE 2

|  | avg. Wt % | avg. Wt % | avg. Wt % |
|  | Active ingredient name | | |
|  | pyrasulfotole | mefenpyr | fenoxaprop-ethyl |
| --- | --- | --- | --- |
| 8 weeks @ 0° C. | 5.57 | 3.77 | 9.41 |
| 8 weeks @ room temp. | 5.67 | 3.76 | 9.34 |
| change from 0° C. | 1.71% | −0.17% | −0.69% |
| 8 weeks @ 40° C. | 5.53 | 3.74 | 9.00 |
| change from 0° C. | −0.82% | −0.65% | −4.31% |
| 8 weeks @ 50° C. | 5.51 | 3.72 | 8.58 |
| change from 0° C. | −1.12% | −1.17% | −8.83% |

COMPARATIVE EXAMPLE 2

A mixture of fenoxaprop-ethyl, mefenpyr, pyrasulfotole, and fillers was prepared in similar manner as in Table 1 but without a buffer system of the invention (see Table 3).

TABLE 3

| INGREDIENTS |
| --- |
| Pyrasulfotole (99% pure) |
| Mefenpyr (94.8% pure) |
| Fenoxyprop-ethyl (94% pure) |
| alkyl alcohol ethoxylate |

TABLE 3-continued

| INGREDIENTS |
| --- |
| [2] benzene sulfonic acid calcium salt |
| [3] epoxidized soy oil |
| [4] ethoxylated sulfate |
| Propylene Carbonate |
| [5] aromatic organic solvent |

[1] Genopol X-060 commercially available from Clariant Corporation.
[2] Ninate 401A commercially available from Stepan Company.
[3] Edenol D81/Vikoflex 7170 commercially available from Clariant Corporation.
[4] Soprophor 4D384 commercially available from Rhodia Corporation.
[5] A150 commercially available from Exxon Corporation.

The mixture was tested for long-term storage stability by subjecting separate samples to different temperatures for eight weeks. The following test results were obtained and shown in Table 4.

TABLE 4

|  | avg. Wt % | avg. Wt % | avg. Wt % |
|  | Active ingredient name | | |
|  | pyrasulfotole | mefenpyr | fenoxaprop-ethyl |
| --- | --- | --- | --- |
| 8 weeks @ 0° C. | 4.76 | 3.81 | 8.20 |
| 8 weeks @ room temp. | 4.75 | 4.01 | 6.49 |
| change from 0° C. | −0.21% | +5.24% | −20.85% |
| 8 weeks @ 40° C. | 4.69 | 3.85 | 2.64 |
| change from 0° C. | −1.47% | −1.05% | −67.80% |
| 8 weeks @ 50° C. | 4.54 | 3.97 | 0.91 |
| change from 0° C. | −4.62% | −4.20% | −88.90% |

As can be seen from Table 4, there was a significant drop in the concentration of fenoxaprop-ethyl without the buffer system of the invention.

What is claimed is:

1. A herbicidal composition, comprising: (a) a fenoxaprop ester herbicide; and (b) a buffer system consisting essentially of a tertiary amine and one or more weak acid herbicides comprising pyrasulfotole.

2. The herbicidal composition of claim 1, further comprising at least one safener.

3. The herbicidal composition of claim 2, wherein the safener comprises mefenpyr.

4. The herbicidal composition of claim 1, wherein the buffer system maintains the composition at a pH of from 4 to 8.

5. The herbicidal composition of claim 4, wherein the buffer system maintains the composition at a pH of from 5.8 to 7.5.

6. The herbicidal composition of claim 1, wherein the herbicidal composition is selected from the group consisting of an emulsifiable concentrate, suspension concentrate, suspoemulsion and a solution.

7. The herbicidal composition of claim 1, wherein the herbicidal composition further comprises at least one surfactant.

8. The herbicidal composition of claim 1, wherein the amine is a tertiary amine or protonated tertiary amine selected from the group consisting of
   a) a trialkylamine selected from triethanolamine, triisopropanolamine, triethylamine, trimethylamine, tripropylamine, triisopropylamine, 1-octaneamine-N,N-dimethyl, N,N-dimethylcyclohexanamine, N,N-dimethyl-1-hexadecylamine, 1-dodeccanamine-N,N-dimethyl, ethyldiethanolamine, hexamethylenetetramine, N,N, N'',N''-tetrakis-(2-hydroxypropyl) ethylene diamine, dicocoalkyl-methylamine, didecylmethylamine, tridodecyamine, trihexadecylamine;
b) a monoalkyldimethylamine selected from the group consisting of dodecyldimethylamine, hexadecyl-dimethylamine, octadecyl-dimethylamine, cocoalkyl-dimethylamine, soyalkyl-dimethylamine, soyaalkyl-dimethylamine, tallowalkyl-dimethylamine, hydrogenated tallowalkyl-dimethylamine, cottonseed alkyl-dimethylamine;
c) an ethoxylated alkylamine selected from the group consisting of ethoxylated (n) cocoalkylamine, ethoxylated (n) tallowalkylamine, ethoxylated (n) soyaalkylamine, ethoxylated cottonseed amine, oleyl amine ethoxylate, ethoxylated (n) octadecylamine, wherein the ethoxy group numbers of n may be from 1 to 60;
d) an ethoxylated diamine selected from the group consisting of ethoxylated(n) N-tallow-1,3-diaminopropane, ethoxylated(n) N-tallow-1,3-diaminopropane, ethoxylated(n) N-tallow-1,3-diaminopropane, N,N-bis[α-ethyl-(.omega.-hydroxypoly(oxyethylene)alkylamine wherein the poly(oxyethylene) content is an average 3 moles and the alkyl groups (C14-C18) are derived from tallow, or from soybean or cottonseed oil acids, or other crop or vegetable seeds oil acids;
e) N,N-bis(2-hydroxyethyl)alkylamine, where the alkyl groups (C8-C18) are derived from coconut, cottonseed, soya, or tallow acids or other crops or vegetable seed acids;
f) N,N-Bis 2-(.omega.-hydroxypolyoxyethylene)ethyl] alkylamine; the reaction product of 1 mole N,N-bis(2-hydroxyethyl)alkylamine and 3-60 moles of ethylene oxide, where the alkylgroup (C8-C18) is derived from coconut, cottonseed, soya, or tallow acids or other crop or vegetable seed acids;
g) N,N-Bis-2-(.omega.-hydroxypolyoxyethylene/polyoxypropylene)ethyl alkylamine; the reaction product of 1 mole of N,N-bis(2-hydroxyethyl alkylamine) and 3-60 moles of ethylene oxide and propylene oxide, where the alkyl group (C8-C18) is derived from coconut, cottonseed, soya, or tallow acids or other crop seeds or, vegetable seeds acids; and
h) N,N'-Bis,(2-hydroxyethyl)-C12-C18 alkylamine, N,N'-bis(polyoxyethylene)cetylamine, N,N'-Bis(polyoxyethylene)oleylamine, N,N'-bis(polyoxyethylene)stearylamine, N,N'-dinitropentamethylenetetramine, ethoxylated abietylamine.

9. A herbicidal composition, consisting essentially of: (a) a fenoxaprop ester herbicide; and (b) a buffer system consisting essentially of a tertiary amine and one or more weak acid herbicides comprising pyrasulfotole.

10. The herbicidal composition of claim 1, wherein the tertiary amine is a triethanolamine.

11. The herbicidal composition of claim 1, wherein the tertiary amine is a trialkylamine.

12. The herbicidal composition of claim 1, wherein the tertiary amine is a monoalkyldimethylamine.

13. The herbicidal composition of claim 1, wherein the tertiary amine is an ethoxylated alkylamine.

14. The herbicidal composition of claim 1, wherein the tertiary amine is a an ethoxylated diamine.

15. The herbicidal composition of claim 1, wherein the tertiary amine is a N,N-bis(2-hydroxyethyl)alkylamine.

16. The herbicidal composition of claim 1, wherein the tertiary amine is a N,N-Bis2-(.omega.-hydroxypolyoxyethylene)ethyl)alkylamine.

17. The herbicidal composition of claim 1, wherein the tertiary amine is a N,N-Bis-2-(.omega.-hydroxypolyoxyethylene/polyoxypropylene)ethyl alkylamine.

18. The herbicidal composition of claim 1, wherein the tertiary amine is a N,N'-Bis,(2-hydroxyethyl)-C12-C18 alkylamine.

19. The herbicidal composition of claim 1, wherein the buffer system consists of a tertiary amine and one or more weak acids comprising pyrasulfotole.

20. The herbicidal composition of claim 9, wherein the buffer system consists of a tertiary amine and one or more weak acid herbicides comprising pyrasulfotole.

* * * * *